United States Patent
Gilmartin et al.

(10) Patent No.: US 11,986,407 B2
(45) Date of Patent: *May 21, 2024

(54) STENT

(71) Applicant: BOSTON SCIENTIFIC SCIMED, INC., Maple Grove, MN (US)

(72) Inventors: Gary Gilmartin, Mayo (IE); Martyn G. Folan, Galway (IE); Geraldine Toner, Raphoe (IE); Paul E. Tierney, Galway (IE); David Collins, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/963,764

(22) Filed: Oct. 11, 2022

(65) Prior Publication Data
US 2023/0041864 A1 Feb. 9, 2023

Related U.S. Application Data

(63) Continuation of application No. 17/412,428, filed on Aug. 26, 2021, which is a continuation of application
(Continued)

(51) Int. Cl.
*A61F 2/90* (2013.01)
*A61F 2/86* (2013.01)
(Continued)

(52) U.S. Cl.
CPC ............ *A61F 2/90* (2013.01); *A61F 2/86* (2013.01); *A61F 2/88* (2013.01);
(Continued)

(58) Field of Classification Search
None
See application file for complete search history.

(56) References Cited

U.S. PATENT DOCUMENTS

| 5,064,435 A | 11/1991 | Porter |
| 5,133,732 A | 7/1992 | Wiktor |

(Continued)

FOREIGN PATENT DOCUMENTS

| EP | 1258229 A1 | 11/2002 |
| GB | 2378137 A | 2/2003 |

(Continued)

OTHER PUBLICATIONS

International Search Report and Written Opinion dated Aug. 29, 2019 for International Application No. PCT/US2019/026407.
(Continued)

*Primary Examiner* — Rebecca S Preston
(74) *Attorney, Agent, or Firm* — Seager, Tufte & Wickhem, LLP

(57) ABSTRACT

An illustrative stent may comprise an elongated tubular member having a first end and a second end and an intermediate region disposed therebetween. The elongated tubular member configured to move between a collapsed configuration and an expanded configuration. The elongated tubular member may comprise at least one twisted filament, such as a knitted filament having a plurality of twisted knit stitches with intermediate rung portions extending between adjacent twisted knit stitches, or a plurality of helical filaments twisted with a plurality of longitudinal filaments.

19 Claims, 11 Drawing Sheets

Related U.S. Application Data

No. 16/378,272, filed on Apr. 8, 2019, now Pat. No. 11,266,517.

(60) Provisional application No. 62/655,025, filed on Apr. 9, 2018.

(51) Int. Cl.
*A61F 2/88* (2006.01)
*A61F 2/04* (2013.01)

(52) U.S. Cl.
CPC . *A61F 2002/045* (2013.01); *A61F 2210/0014* (2013.01); *A61F 2220/0075* (2013.01); *A61F 2230/0045* (2013.01); *A61F 2250/0007* (2013.01); *A61F 2250/001* (2013.01); *A61F 2250/0012* (2013.01); *A61F 2250/0017* (2013.01); *A61F 2250/0098* (2013.01)

(56) References Cited

U.S. PATENT DOCUMENTS

| | | | |
|---|---|---|---|
| 5,234,456 A | 8/1993 | Silvestrini | |
| 5,366,504 A | 11/1994 | Andersen et al. | |
| 5,628,788 A | 5/1997 | Pinchuk | |
| 5,800,519 A | 9/1998 | Sandock | |
| 5,876,445 A | 3/1999 | Andersen et al. | |
| 6,264,689 B1 | 7/2001 | Colgan et al. | |
| 6,305,436 B1 | 10/2001 | Andersen et al. | |
| 6,485,515 B2 | 11/2002 | Strecker | |
| 6,494,907 B1 | 12/2002 | Bulver | |
| 6,520,983 B1 | 2/2003 | Colgan et al. | |
| 6,540,773 B2 | 4/2003 | Dong | |
| 6,554,855 B1 | 4/2003 | Dong | |
| 6,893,457 B2 | 5/2005 | Dong | |
| 6,939,372 B2 | 9/2005 | Dong | |
| 7,011,676 B2 | 3/2006 | Dong | |
| 7,198,638 B2 | 4/2007 | Dong | |
| 7,364,587 B2 | 4/2008 | Dong et al. | |
| 7,594,928 B2 | 9/2009 | Headley, Jr. et al. | |
| D612,499 S | 3/2010 | Ondracek et al. | |
| 7,854,756 B2 | 12/2010 | Shaw | |
| 8,435,285 B2 | 5/2013 | Shank et al. | |
| 8,974,516 B2 | 3/2015 | Hyodoh et al. | |
| 9,265,635 B2 | 2/2016 | Walak | |
| 9,498,319 B2 | 11/2016 | Walak | |
| 9,849,009 B2 | 12/2017 | Thompson | |
| 9,849,010 B2 | 12/2017 | Thompson | |
| 11,266,517 B2 * | 3/2022 | Gilmartin | D04B 1/225 |
| 2002/0022875 A1 | 2/2002 | Strecker | |
| 2003/0040789 A1 | 2/2003 | Colgan et al. | |
| 2005/0049682 A1 | 3/2005 | Leanna et al. | |
| 2005/0110214 A1 | 5/2005 | Shank et al. | |
| 2006/0058862 A1 | 3/2006 | Dong et al. | |
| 2009/0005855 A1 | 1/2009 | Goto et al. | |

FOREIGN PATENT DOCUMENTS

| | | |
|---|---|---|
| JP | H09512460 A | 12/1997 |
| JP | 2005168757 A | 6/2005 |
| JP | 2010522015 A | 7/2010 |

OTHER PUBLICATIONS

Machine translation of JP2005168757, pp. 1-4, accessed Aug. 26, 2021. https://worldwide.espacenet.com/patent/search/family/034732792/publication/JP2005168757A?q=pn%BDJP2005168757A (Year: 2021).

* cited by examiner

STENT

CROSS-REFERENCE TO RELATED APPLICATIONS

This application is a continuation of co-pending U.S. application Ser. No. 17/412,428, filed Aug. 26, 2021, which is a continuation of U.S. application Ser. No. 16/378,272, filed Apr. 8, 2019, now U.S. Pat. No. 11,266,517, which claims the benefit of priority of U.S. Provisional Application No. 62/655,025, filed Apr. 9, 2018, the entire disclosures of which are hereby incorporated by reference.

TECHNICAL FIELD

The present disclosure pertains to medical devices, methods for manufacturing medical devices, and uses thereof. More particularly, the present disclosure pertains to a stent for implantation in a body lumen, and associated methods.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods.

SUMMARY

This disclosure provides design, material, manufacturing method, and use alternatives for medical devices. An example medical device may include a stent.

In a first example, a stent may comprise an elongated tubular member comprising at least one knitted filament having a plurality of twisted knit stitches with intermediate rung portions extending between adjacent twisted knit stitches, the elongated tubular member configured to move between a collapsed configuration and an expanded configuration. In in the collapsed configuration the plurality of twisted knit stitches have a first profile and in the expanded configuration the plurality of twisted knit stitches have a second profile different from the first profile.

Alternatively or additionally to any of the examples above, in another example, a length of the intermediate rung portions in the collapsed configuration may be less than a length of the intermediate rung portions in the expanded configuration.

Alternatively or additionally to any of the examples above, in another example, at least some of the plurality of twisted knit stitches may be suspended from a twisted knit stitch in a preceding row.

Alternatively or additionally to any of the examples above, in another example, the plurality of twisted knit stitches may each include a loop portion and an overlapping base region.

Alternatively or additionally to any of the examples above, in another example, at least some of the plurality of twisted knit stitches may be suspended from an intermediate rung portion of a preceding row.

Alternatively or additionally to any of the examples above, in another example, the elongated tubular member may comprise a plurality of rows, wherein some of the plurality of rows have a first number of twisted knit stitches and some of the plurality of rows may have a second number of twisted knit stitches less than the first number of twisted knit stitches.

Alternatively or additionally to any of the examples above, in another example, the elongated tubular member may have at least a first portion and a second portion, the second portion may have a lower radial force in the expanded configuration than the first portion.

In another example, a stent may comprise an elongated tubular member comprising a plurality of longitudinal filaments extending generally along a longitudinal axis of the elongated tubular member, a first helical filament extending in a first helical direction, and a second helical filament extending in a second helical direction opposite to the first helical direction, the plurality of longitudinal filaments, first helical filament, and second helical filament overlapping to form a plurality of cell. The longitudinal filaments are intermittently helically wrapped with one of the first or second helical filaments to form a plurality of interlocking joints, the interlocking joints extending at a non-parallel angle relative to the longitudinal axis of the elongated tubular member.

Alternatively or additionally to any of the examples above, in another example, the plurality of cells may have a generally hexagonal shape having six sides defined by a length.

Alternatively or additionally to any of the examples above, in another example, the interlocking joints may be positioned between adjacent sides of the cell.

Alternatively or additionally to any of the examples above, in another example, the first helical filament and the second helical filament may cross at one or more cross points.

Alternatively or additionally to any of the examples above, in another example, the one or more cross points may be free from an interlocking joint.

Alternatively or additionally to any of the examples above, in another example, the longitudinal filaments may be uniformly spaced about a circumference of the elongated tubular body.

Alternatively or additionally to any of the examples above, in another example, the longitudinal filaments may be unequally spaced about a circumference of the elongated tubular body.

Alternatively or additionally to any of the examples above, in another example, the interlocking joints may extend at an angle in the range of 40° to about 50° relative to the longitudinal axis of the elongated tubular member.

In another example, a stent may comprise an elongated tubular member comprising a plurality of knitted rows, each row including a plurality of loops having a loop portion and a twisted base portion with intermediate rung portions extending between adjacent loops, the elongated tubular member configured to move between a collapsed configuration and an expanded configuration. At least some of the plurality of loops may be configured to be suspended from the twisted base portion of a loop in a preceding row.

Alternatively or additionally to any of the examples above, in another example, a length of the intermediate rung portions in the collapsed configuration may be less than a length of the intermediate rung portions in the expanded configuration.

Alternatively or additionally to any of the examples above, in another example, the elongated tubular member may have at least a first portion and a second portion, the second portion may have a lower radial force in the expanded configuration than the first portion.

Alternatively or additionally to any of the examples above, in another example, at least some of the plurality of loops may be suspended from an intermediate rung portion of a preceding row.

Alternatively or additionally to any of the examples above, in another example, some of the plurality of rows may have a first number of loops and some of the plurality of rows may have a second number of loops less than the first number of loops.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments in connection with the accompanying drawings, in which.

Figure 1:
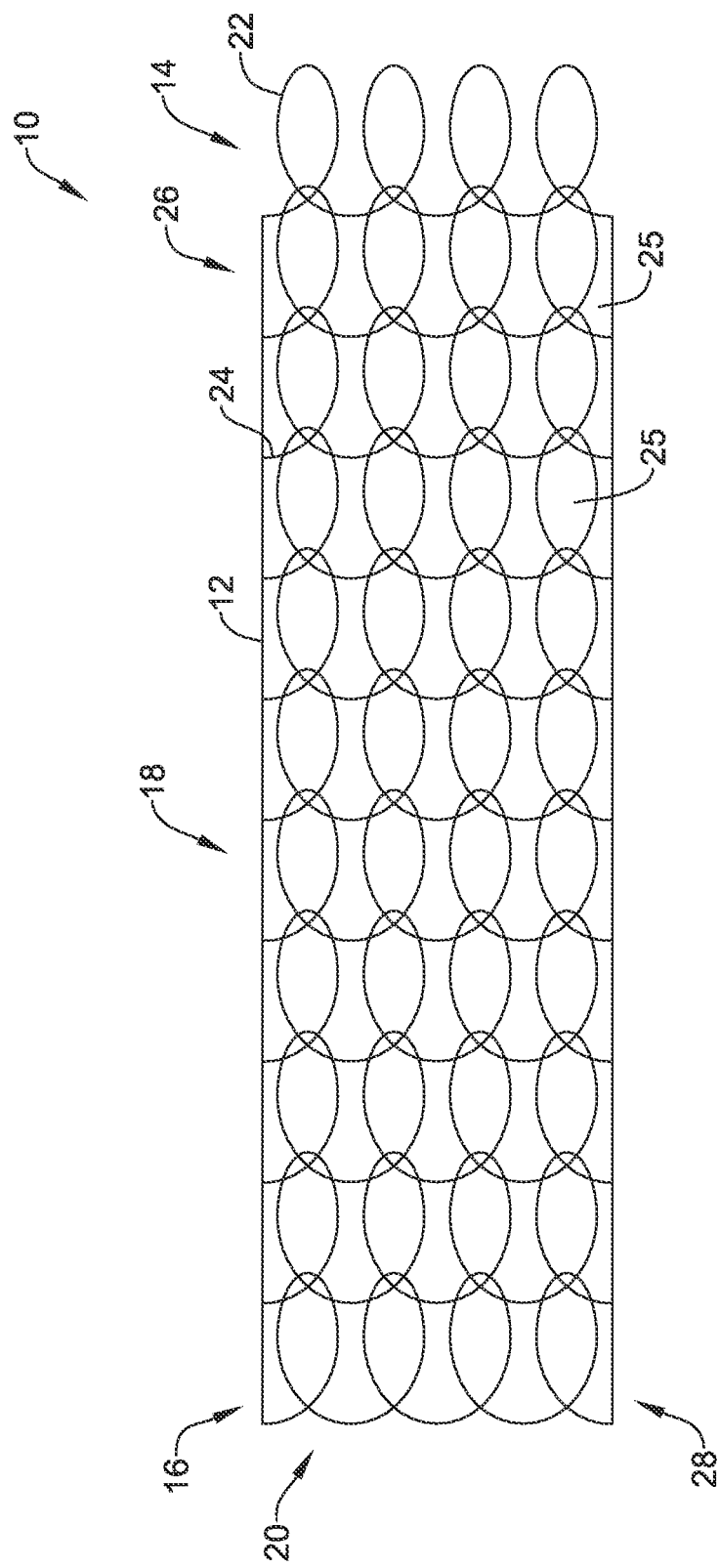
FIG. 1 is a side view of an illustrative stent.

While the disclosure is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

In some instances, it may be desirable to provide an endoluminal implant, or stent, that can deliver luminal patency in a patient with an esophageal stricture or other medical condition. Such stents may be used in patients experiencing dysphagia, sometimes due to esophageal cancer. An esophageal stent may allow a patient to maintain nutrition via oral intake during cancer treatment or palliation periods. Some stents have a woven or knitted configuration to provide good radial strength with minimal foreshortening which may be desirable in esophageal and trachea-bronchial applications as well as some post-bariatric surgery applications. However, some knitted stent designs may be difficult to constrain, especially into a coaxial delivery system and thus may be delivered using a system which may not offer a method of recapture. What may be desirable is an alternative knitted stent that is capable of delivery via a coaxial delivery system while having similar radial forces and foreshortening as previous knitted stent configurations While the embodiments disclosed herein are discussed with reference to esophageal stents, it is contemplated that the stents described herein may be used and sized for use in other locations such as, but not limited to: bodily tissue, bodily organs, vascular lumens, non-vascular lumens and combinations thereof, such as, but not limited to, in the coronary or peripheral vasculature, trachea, bronchi, colon, small intestine, biliary tract, urinary tract, prostate, brain, stomach and the like.

FIG. 1 illustrates a side view of an illustrative endoluminal implant 10, such as, but not limited to, a stent. In some instances, the stent 10 may be formed from an elongated tubular member 12. While the stent 10 is described as generally tubular, it is contemplated that the stent 10 may take any cross-sectional shape desired. The stent 10 may have a first, or proximal end 14, a second, or distal end 16, and an intermediate region 18 disposed between the first end 14 and the second end 16. The stent 10 may include a lumen 20 extending from a first opening adjacent the first end 14 to a second opening adjacent to the second end 16 to allow for the passage of food, fluids, etc.

The stent 10 may be expandable from a first radially collapsed configuration (not explicitly shown) to a second radially expanded configuration. In some cases, the stent 10 may be deployed to a configuration between the collapsed configuration and a fully expanded configuration. The stent 10 may be structured to extend across a stricture and to apply a radially outward pressure to the stricture in a lumen to open the lumen and allow for the passage of foods, fluids, air, etc.

The proximal end 14 of the stent 10 may include a plurality of loops 22. The loops 22 may be configured to receive a retrieval tether or suture interwoven therethrough, or otherwise passing through one or more of the loops 22. The retrieval suture may be used to collapse and retrieve the stent 10, if so desired. For example, the retrieval suture may be pulled like a drawstring to radially collapse the proximal end 14 of the stent 10 to facilitate removal of the stent 10 from a body lumen.

The stent 10 may have a knitted structure, fabricated from a single filament 24 interwoven with itself and defining open cells 25. In some cases, the filament 24 may be a monofilament, while in other cases the filament 24 may be two or more filaments wound, braided, or woven together. In some instances, an inner and/or outer surface of the stent 10 may be entirely, substantially or partially, covered with a polymeric covering or coating. The covering or coating may extend across and/or occlude one or more, or a plurality of the cells defined by the struts or filaments 24. The covering or coating may help reduce food impaction and/or tumor or tissue ingrowth.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, Nitinol and Elgiloy®. Depending on the material selected for construction, the stent 10 may be self-expanding (i.e., configured to automatically radially expand when unconstrained). In some embodiments, fibers may be used to make the stent 10, which may be composite fibers, for example, having an outer shell made of Nitinol having a platinum core. It is further contemplated the stent 10 may be formed from polymers including, but not limited to, polyethylene terephthalate (PET). In some embodiments, the stent 10 may be self-expanding while in other embodiments, the stent 10 may be expand by an expansion device (such as, but not limited to a balloon inserted within the lumen 20 of the stent 10). As used herein the term "self-expanding" refers to the tendency of the stent to return to a preprogrammed diameter when unrestrained from an external biasing force (for example, but not limited to a delivery catheter or sheath). The stent 10 may include a one-way valve, such as an elastomeric slit valve or duck bill valve, positioned within the lumen 20 thereof to prevent retrograde flow of gastrointestinal fluids.

In some instances, in the radially expanded configuration, the stent 10 may include a first end region 26 proximate the proximal end 14 and a second end region 28 proximate the second end 16. In some embodiments, the first end region 26 and the second end region 28 may include retention features or anti-migration flared regions (not explicitly shown) having enlarged diameters relative to the intermediate portion 18. The anti-migration flared regions, which may be positioned adjacent to the first end 14 and the second end 16 of the stent 10, may be configured to engage an interior portion of the walls of the esophagus or other body lumen. In some embodiments, the retention features, or flared regions may have a larger diameter than the cylindrical intermediate region 18 of the stent 10 to prevent the stent 10 from migrating once placed in the esophagus or other body lumen. It is contemplated that a transition from the cross-sectional area of the intermediate region 18 to the retention features or flared regions may be gradual, sloped, or occur in an abrupt step-wise manner, as desired.

In some embodiments, the first anti-migration flared region may have a first outer diameter and the second anti-migration flared region may have a second outer diameter. In some instances, the first and second outer diameters may be approximately the same, while in other instances, the first and second outer diameters may be different. In some embodiments, the stent 10 may include only one or none of the anti-migration flared regions. For example, the first end region 26 may include an anti-migration flare while the second end region 28 may have an outer diameter similar to the intermediate region 18. It is further contemplated that the second end region 28 may include an anti-migration flare while the first end region 26 may have an outer diameter similar to an outer diameter of the intermediate region 18. In some embodiments, the stent 10 may have a uniform outer diameter from the first end 14 to the second end 16. In some embodiments, the outer diameter of the intermediate region 18 may be in the range of 15 to 25 millimeters. The outer diameter of the anti-migration flares may be in the range of 20 to 30 millimeters. It is contemplated that the outer diameter of the stent 10 may be varied to suit the desired application.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, Nitinol and Elgiloy®. Depending on the material selected for construction, the stent 10 may be self-expanding or require an external force to expand the stent 10. In some embodiments, composite filaments may be used to make the stent 10, which may include, for example, an outer shell or cladding made of Nitinol and a core formed of platinum or other radiopaque material. It is further contemplated the stent 10 may be formed from polymers including, but not limited to, polyethylene terephthalate (PET). In some instances, the filaments of the stent 10, or portions thereof, may be bioabsorbable or biodegradable, while in other instances the filaments of the stent 10, or portions thereof, may be biostable.

Figure 2:
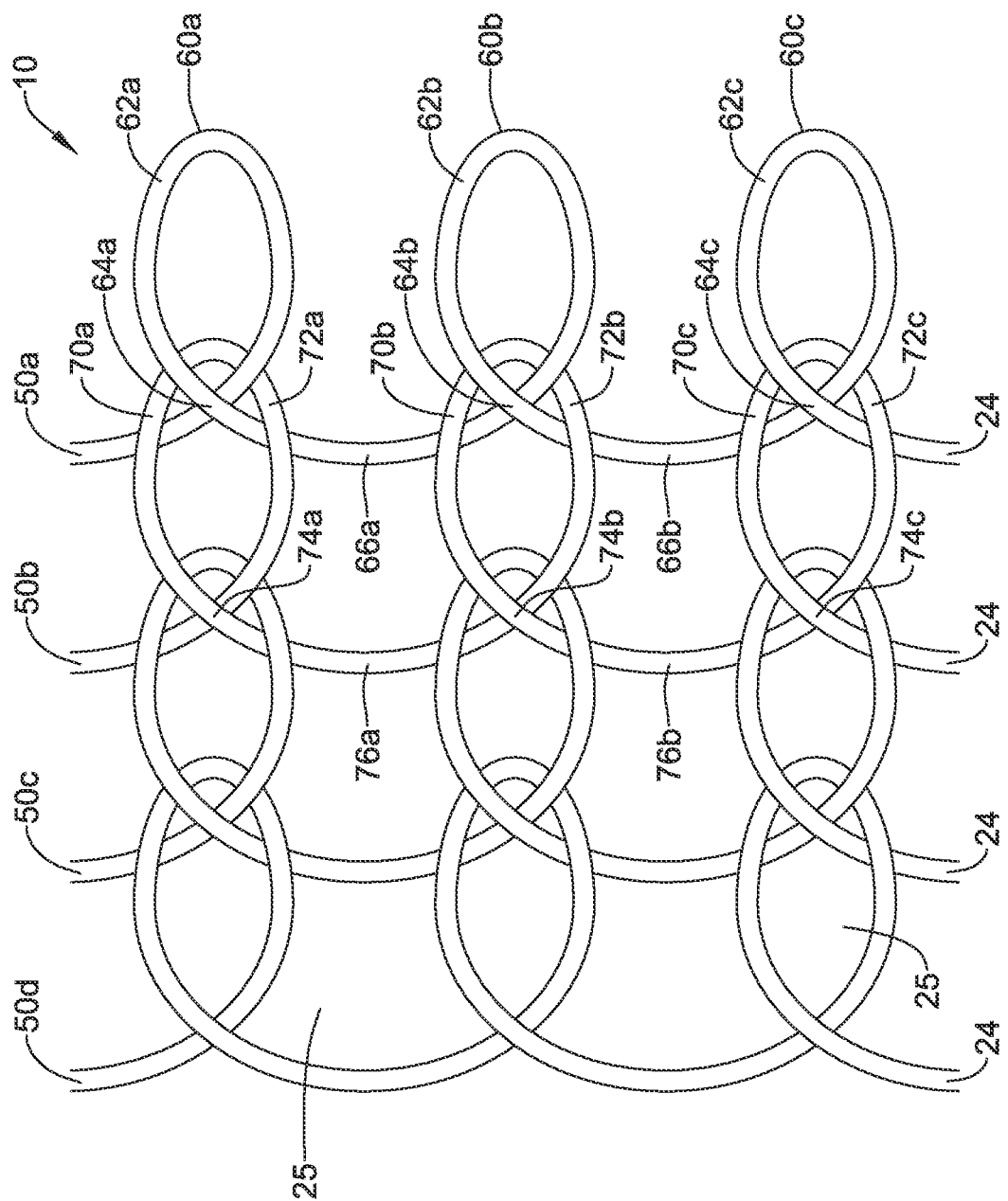
FIG. 2 is an enlarged side view of a portion of the illustrative stent of FIG. 1.

FIG. 2 illustrates enlarged side view of the knitted configuration of the stent 10. The stent 10 may include a plurality of rows 50a, 50b, 50c, 50d (collectively, 50) extending circumferentially about the stent 10. The stent 10 may include any number of rows 50 desired. For example, the number of rows 50 may be selected to achieve a desired length of the stent 10. The uppermost, or first, row 50a may be unsecured and active. In some instances, the first row 50a may include a plurality of loops 60a, 60b, 60c (collectively, 60). The loops 60 may each include a loop portion 62a, 62b, 62c (collectively, 62) and an overlapping base portion 64a, 64b, 64c (collectively, 64). The overlapping base portion 64a, 64b, 64c is understood as the portion of the loops 60 in which one segment of the filament overlaps or crosses over a second segment of the filament, with the segment of the filament forming the loop portion 62a, 62b, 62c extending therebetween. Adjacent loops 60 may be interconnected by a rung section 66a, 66b (collectively, 66). For example, a first rung section 66a may extend between the base portion 64a of the first loop 60a and the second base portion 64b of the second loop 60b. The next row 50b may be suspended from the loops 60 of the first row 50a. For example, the second row 50b may include a plurality of loops 70a, 70b, 70c (collectively, 70) each including a loop portion 72a, 72b, 72c (collectively, 72) and a base portion 74a, 74b, 74c (collectively, 74). Adjacent loops 70 may be interconnected by a rung section 76a, 76b (collectively, 76). As the stent 10 is knitted, the loop portion 72 may be wrapped about the base portion 64 of the preceding row 50a.

It is contemplated that a single row 50 may be formed at a time. For example, the rows may be formed in succession with a subsequent row (e.g., row 50b) being formed after the preceding row (e.g., row 50a) has formed a complete rotation. While not explicitly shown, the loops 60 of the first row 50a may be wrapped about a section of the filaments 24 free from loops. As described herein, the loops 70 of the second row 50b may be wrapped about the base portion 64 of the loops 60 the preceding row 50a. For example, the filament 24 may be knitted such that it extends from the first rung section 76a, is wrapped about the base portion 64b of the preceding row 50a, crosses back over itself to form base section 74b and continues to the next rung section 76b. It is contemplated that the loop portion 70 may be positioned on a first side of the rungs 66a, 66b and on a second opposite side of the loop portion 62b. In other words, the filament 24 may be wound such that it extends on top of the second rung portion 66b, behind the base portion 64b, and over the first rung portion 66a before crossing over itself to form the base portion 74b of the loop 70b of the second row 50b. The reverse configuration is also contemplated in which the filament 24 may be wound such that it extends behind the second rung portion 66b, over or on top of the base portion 64b, and behind the first rung portion 66a before crossing over itself to form the base portion 74b of the loop 70b of the second row 50b.

Figure 3:
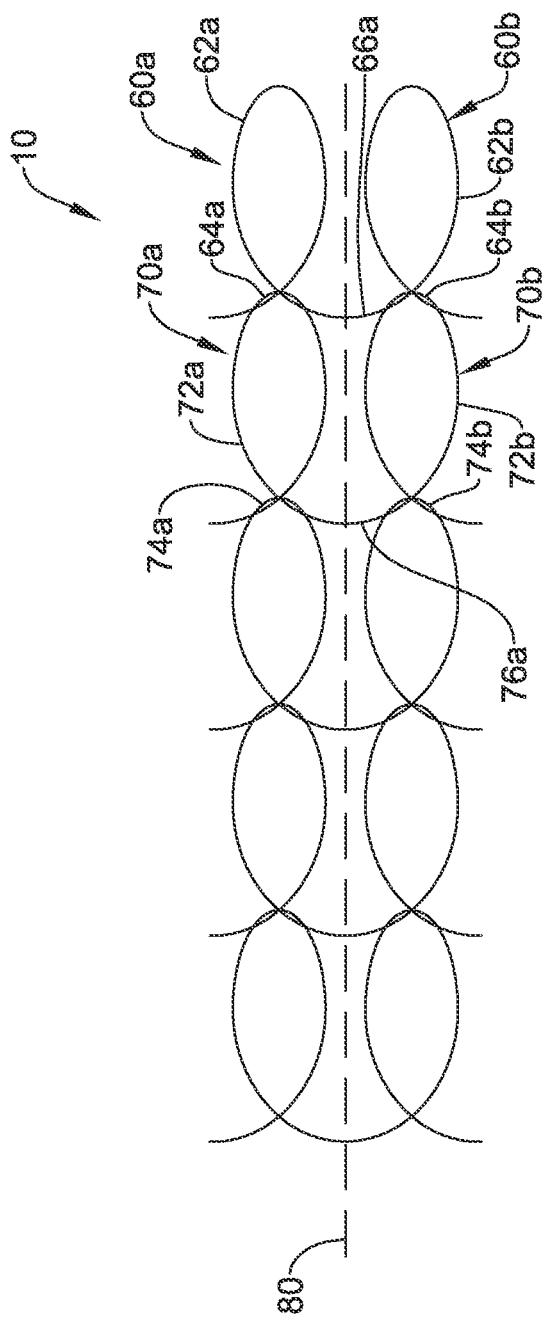
FIG. 3 is a partial side view of the illustrative stent of FIG. 1 in an elongated configuration.

The knitted structure of the stent 10 may allow the loop sections 62, 72 to lengthen such that the cells 25 and/or loop sections 62, 72 have a first profile when the stent 10 is in the expanded configuration and the second profile, different from the first profile, when the stent 10 is in a collapsed delivery configuration. Lengthening of the loop sections 62, 72 may allow the cross-sectional diameter of the stent 10 to be reduced for delivery. To lengthen, the loops 60, 70 use some of the length of the filament 24 from the rungs 66, 76 to elongate. FIG. 3 illustrates a portion of the stent 10 in an elongated configuration. As can be seen, as the loops 60, 70 elongate, the rung material 66, 76 is pulled into the loop portion 62, 72 to allow for loop elongation (e.g., in a direction along a longitudinal axis 80) while the intermediate rung portion 66, 76 is shortened. The rung material 66, 76 may be accessible and readily subsumed into the loop portion 62, 72 due to the twist region 64, 74. This may result in the stent 10 being constrained at lower forces allowing it to be loaded into a coaxial delivery system. It is contemplated that the knit structure of the stent 10 may be less subject to wire breaks due to fatigue from peristaltic motion, when compared to previous knit for stents. The softer curvature of the current knit pattern may allow the loops 60, 70 be easily pursed by external forces which may be applied to the stent 10 by the anatomy.

Figure 4:
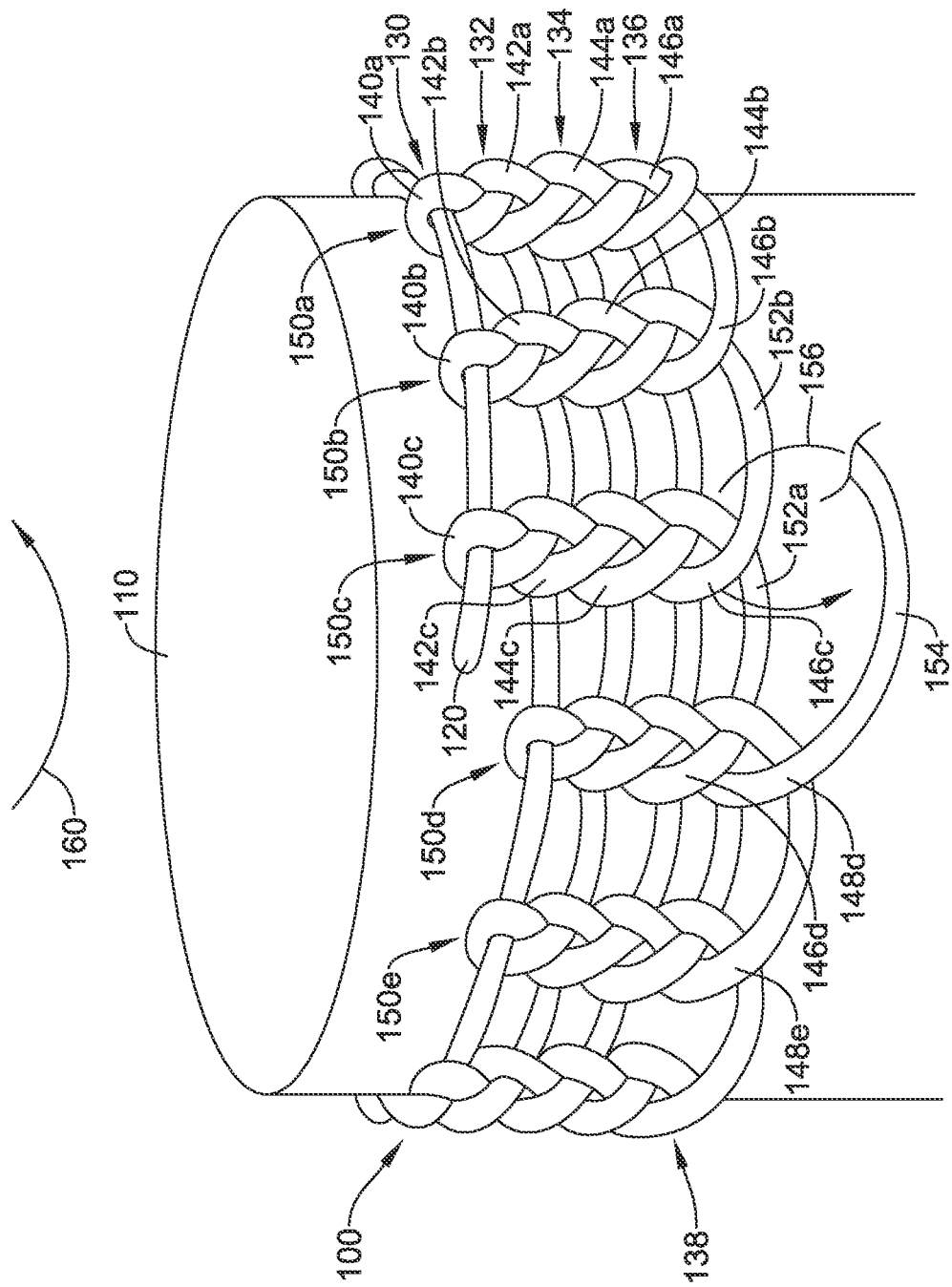
FIG. 4 is an illustrative method of forming a stent.

FIG. 4 illustrates a side view of an illustrative stent 100 being formed about a mandrel 110. The stent 100 may be similar in form and function to the stent 10 described above. The stent 100 may be formed from a single knitted strand or filament 120. In general, the stent 100 is formed by knitting in a single direction. For example, in the embodiments illustrated in FIG. 3, the strand 120 is knitted in a counter-clockwise direction as shown at arrow 160. However, it should be understood that the stent 100 may be formed by knitting in a clockwise direction, as desired. The strand 120 may follow a looped path about the mandrel 110 configured to form a plurality of interconnected loops.

The strand 120 may be manipulated (e.g., knitted) into a plurality of rows 130, 132, 134, 136, 138 each having a plurality of interconnected or intermeshing loops 140a-c, 142a-c, 144a-c, 146a-c, 148d-e. The stent 100 may include as many rows as required to form a stent 100 having the desired length. As described above, the loops may be loosely knit and include interconnecting intermediate rung portions such as the rung portions 152a and 152b interconnecting three loops 146d, 146c, 146b of one of the rows 136. It should be understood that as the stent 100 is formed from a single strand 120, the rows 130, 132, 134, 136, 138 may not be distinct and separate rows but instead form a continuous connection with the preceding and/or following row. It is further contemplated that the stent 100 need not be formed from a single strand 120 but rather may include two or more strands knitted together. In some instances, a loop may be generally aligned with, or suspended from, a loop of the preceding row in a direction generally parallel to a longitudinal axis of the stent 100 (for example, circumferentially aligned along a length of the stent 100). As can be seen, the loop 146b in one row 136 is suspended from the loop 144b in the row 134 above it. Thus, the loops may form axially extending columns or wales 150a-e, although this is not required.

To form the stent 100, an end region 154 of the strand 120 is passed over an intermediate rung portion 152b of a preceding row 136, as shown at arrow 156. The end region 154 of the strand 120 may then be wrapped behind the loop 146c in a direction opposite to the general direction 160 of the overall knit. The end region 154 of the strand 120 may then be passed over a rung portion 152a on opposing side of the loop 146c (relative to the rung portion 152b) before being crossed over itself to complete the loop. The reverse configuration is also contemplated in which the loop passes behind the rung portions 152b, 152a and over the loop 146c. The loops 140a-c, 142a-c, 144a-c, 146a-c, 148d-e may generally take the form of a twisted knit stitch where each individual loop is twisted. It is contemplated that the twisted nature of the loops may create ridges in the outer surface of the stent 100. These ridges may help secure the stent 100 within the body lumen.

Figure 5:
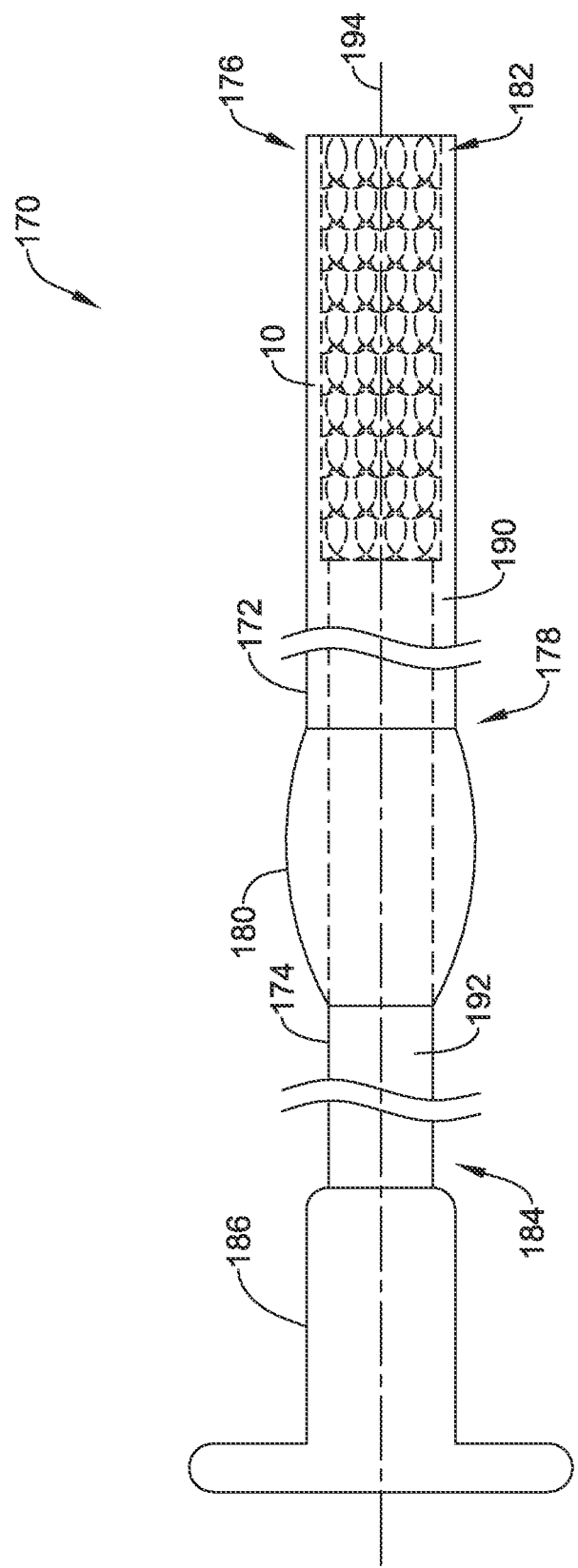
FIG. 5 is a side view of an illustrative delivery system for delivering a stent.

FIG. 5 is a side view of an illustrative delivery system 170 for delivering a stent, such as the stents 10, 100 described herein, to a target region. The delivery system 170 may include an outer or exterior elongate shaft or tubular member 172 and an inner elongate shaft or tubular member 174. The inner tubular member 174 may be slidably disposed within a lumen of the outer tubular member 172. The outer tubular member 172 may extend proximally from a distal end region 176 to a proximal end region 178 configured to remain outside of a patient's body. A first hub or handle 180 may be coupled to the proximal end region 178 of the outer tubular member 172. The inner tubular member 174 may extend proximally from a distal end region 182 to a proximal end region 184 configured to remain outside of a patient's body. A second hub or handle 186 may be coupled to the proximal end region 184 of the inner tubular member 174. In some instances, the distal end region 176 of the outer tubular member 172 may be configured to be atraumatic.

The outer tubular member 172 may include a lumen 190 extending from the distal end region 176 to the proximal end region 178. The lumen 190 may also extend through the first handle 180. The lumen 190 of the outer shaft 172 and the first handle 180 may be configured to slidably receive the inner shaft 174. The inner tubular member 174 may include a lumen 192 extending from the distal end region 182 to the proximal end region 184. The lumen 192 of the inner tubular shaft 174 may also extend through the second handle 186. The lumen 192 of the inner shaft 174 may be configured to receive a guidewire 194, as desired.

The stent 10 may be disposed around a portion of the inner tubular member 174 at or adjacent to the distal end region 182 thereof. When the stent 10 is disposed over the inner tubular member 174, in a collapsed and elongated delivery configuration, the stent 10 may be restrained in a collapsed reduced diameter or delivery configuration by the outer tubular member 172 surrounding the stent 10. In the collapsed configuration, the stent 10 may have a smaller diameter and a longer length than the expanded deployed configuration. The distal end region 176 of the outer tubular member 172 may be positioned such that the outer tubular member 172 surrounds and covers the length of the stent 10 during delivery. The outer tubular member 172 may have sufficient hoop strength to retain the stent 10 in its reduced diameter state.

Figure 6:
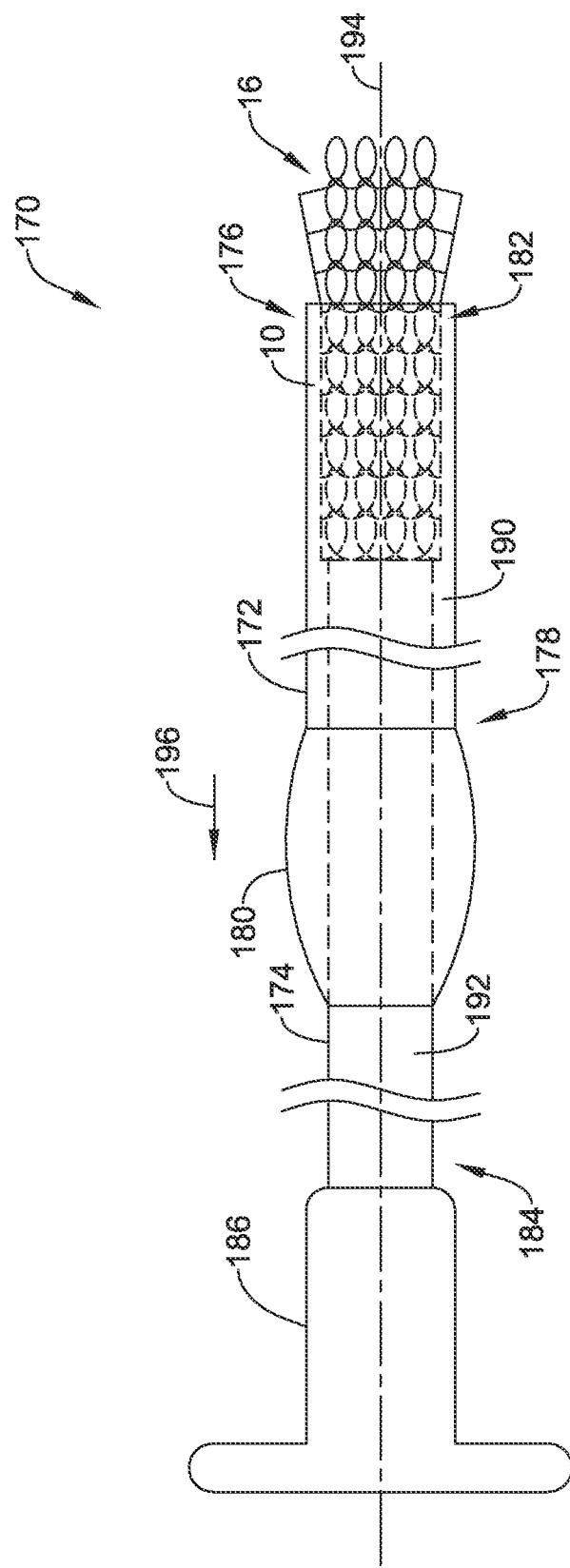
FIG. 6 is a side view of the illustrative delivery system of FIG. 5 the stent in a partially deployed configuration.

FIG. 6 illustrates a side view of the delivery system 170 with the stent 10 in a partially deployed configuration. The delivery system 170 may be advanced through the gastrointestinal tract (or other body lumen), as desired. The delivery system 170 may be advanced with or without the use of a guidewire 194. Once the stent 10 is positioned adjacent to the target region, the restraining forces maintaining the stent 10 in the radially collapsed configuration may be removed to deploy the stent 10.

The stent 10 may be released by actuating the first handle 180 proximally relative to the second handle 186, e.g., by pulling the first handle 180 proximally 226 while maintaining the second handle 186 in a fixed position. Thus, the outer tubular shaft 172 may be retracted proximally relative to the inner tubular shaft 174. In other words, the outer tubular shaft 172 may be proximally retracted while the inner tubular shaft 174 is held stationary. As shown in FIG. 6, as the outer tubular shaft 172 is retracted proximally 196 to uncover the stent 10, the biasing force is removed from the exterior of the stent 10 and the stent 10 assumes its radially expanded, unbiased, deployed configuration. Once the outer tubular member 172 no longer covers the proximal end 14 of the stent 10, the stent 10 may assume its fully deployed configuration, as shown in FIG. 1. The delivery system 170 may then be removed from the body lumen.

Figure 7:
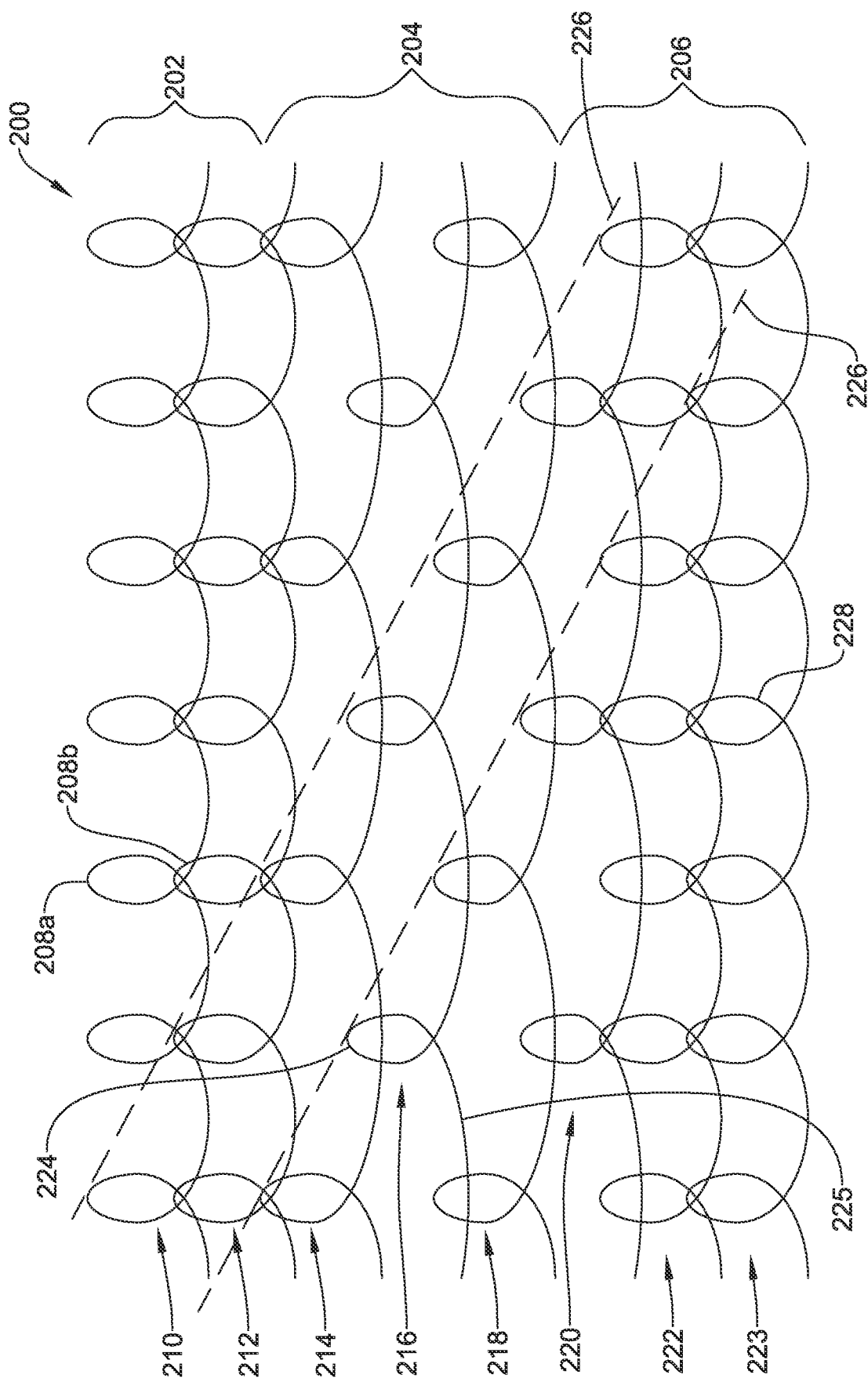
FIG. 7 is a partial side view of another illustrative stent.

FIG. 7 illustrates a side view of another alternative stent 200 having an alternative knitted configuration. The stent may include a first portion 202 including one or more rows 210, 212 where a loop 208b in a row 212 is suspended from every loop 208a in the preceding row 210 in a manner similar to the stents 10, 100 described above. The stent 200 may further include a second or intermediate portion 204 having one or more rows 214, 216, 218, 220 where only every other loop 224 is formed. In the intermediate portion 204, some or all of the loops 224 may be suspended from the intermediate rung portion 225. In some instances, the stent may further include a third portion 206 including one or more rows 222, 223 including the same number of loops 228 as the first portion 202. Is contemplated that the intermediate portion 204 may result in a spiral patterns being formed as shown at dashed lines 226, when the first row 210 include an odd number of loops. The spiral portion 204 may have a lower radial force than the first portion 202 and/or the third portion 206. It is contemplated that the spiral portion 204 need not necessarily be positioned between the first portion 202 and the third portion 206. For example, the stent 200 may include only one of the first portion 202 or the third portion 206.

Figure 8:
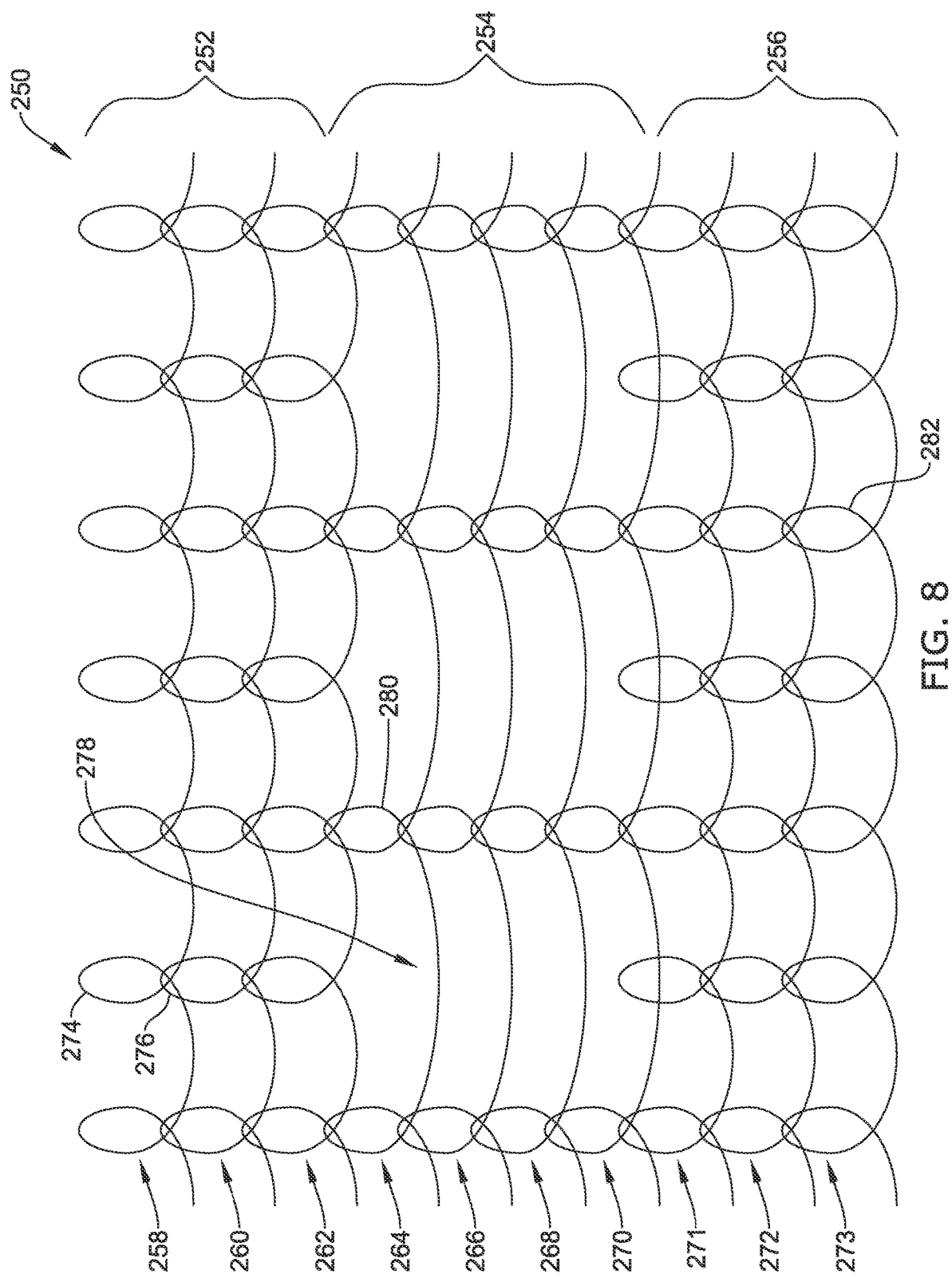
FIG. 8 is a partial side view of another illustrative stent.

FIG. 8 illustrates a side view of another alternative stent 250 having an alternative knitted configuration. The stent may include a first portion 252 including one or more rows 258, 260, 262 where a loop 276 in a row 260 is suspended from every loop 274 in the preceding row 258 in a manner similar to the stents 10, 100 described above. The stent 250 may further include a second or intermediate portion 254 having one or more rows 264, 266, 268, 270 where only every other loop 280 is formed and every other loop 278 is dropped. In other words, the rows 264, 266, 268, 270 in the second portion 254 may have fewer loops 280 than the rows 258, 260, 262 in the first portion 252. In some instances, the stent 250 may further include a third portion 256 including one or more rows 271, 272, 273 including the same number of loops 282 as the first portion 252. It is contemplated that the intermediate portion 254 may have a reduced number of loops 280 (relative to the first and/or third portions 252, 256) which may result in a region having a reduced radial force. This may be beneficial for placing the stent 250 in a region of the anatomy with sharper bends or to possibly afford a wider open section for drainage requirements, among other advantages. As shown in in the third portion 256 the dropped loop 278 may be picked up again, if so desired. In some instances, the stent 250 may end with the second portion 254 when it is desired for the stent 250 to be terminated at a section with reduced radial force. For example, the stent 250 may terminate with the second portion 254 if a softer stent end is required to reduce tissue aggravation.

Figure 9:
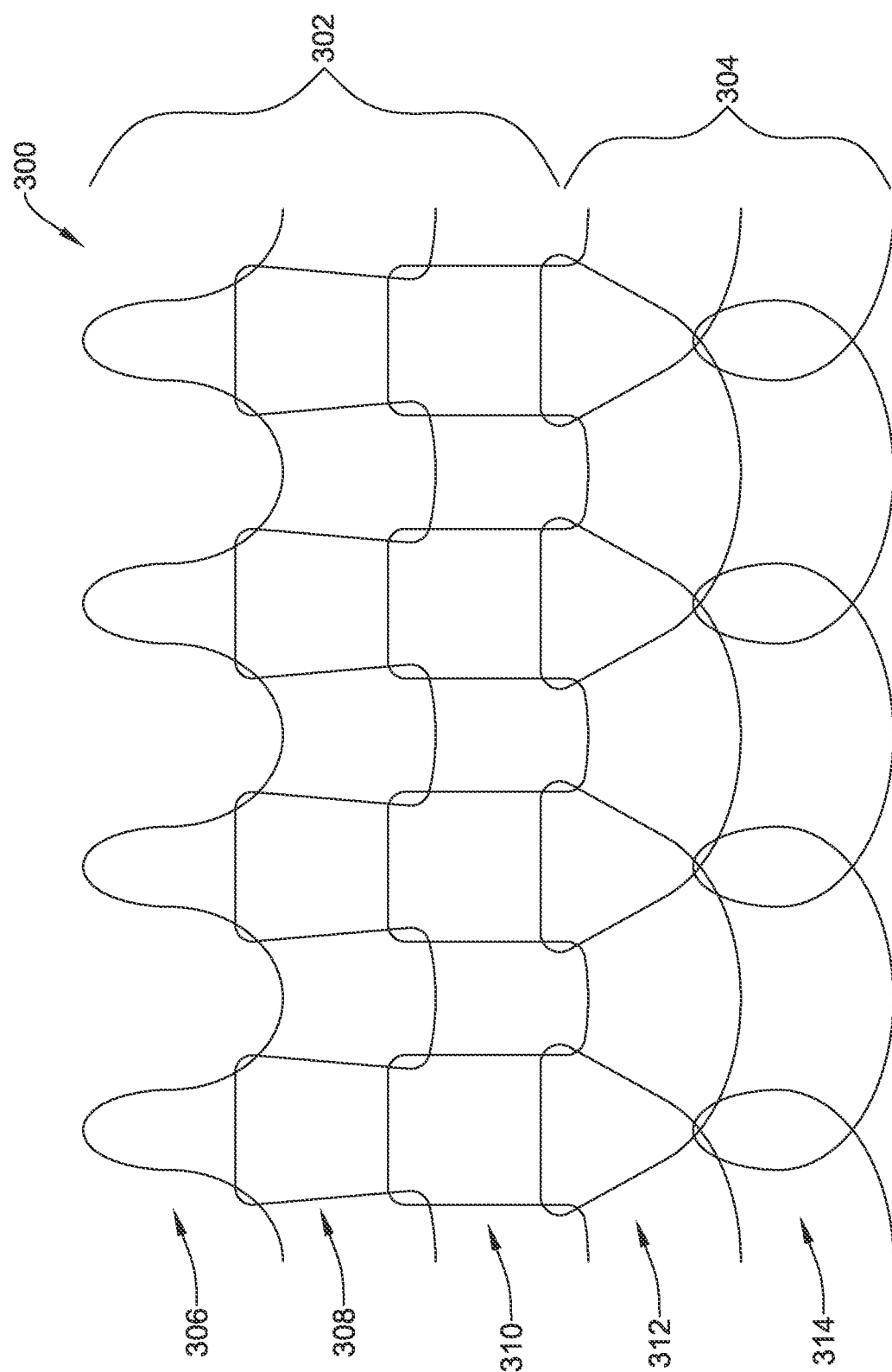
FIG. 9 is a partial side view of another illustrative stent.

FIG. 9 illustrates a side view of another alternative stent 300 having an alternative knitted configuration. The stent 300 may include a first portion 302 having a first knit pattern and the second portion 304 having a second knit pattern different from the first knit pattern. In some embodiments, the first portion 302 may be formed from one or more rows 306, 308, 310 having a stockinette stitch while the second portion 304 may be formed from one or more rows 312, 314 having a twisted knit stitch as described with respect to FIGS. 2-4. It is contemplated that incorporating a hybrid of two or more knit patterns may provide a variable flexibility along a length of the stent 300. This may allow the stent 300 to be more or less compliant with the surrounding anatomy. It is contemplated that the stent 300 may include any number of sections having a different knit pattern desired. For example, the stent 300 may include two, three, four, or more different knit patterns. It is further contemplated that the knit patterns may be arranged in any configuration desired. This may include blocks of rows having a same knit pattern alternating with other blocks of rows having a different knit pattern, alternating rows of different knit patterns, etc.

Figure 10:
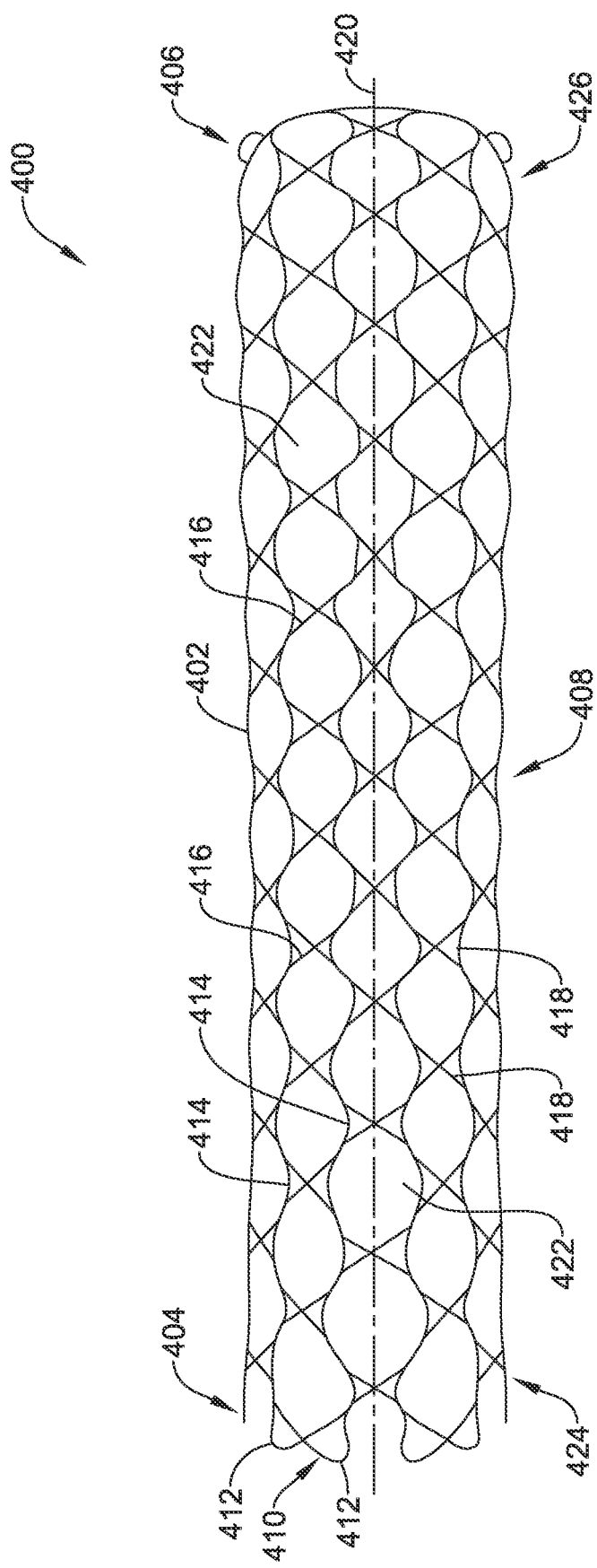
FIG. 10 is a side view of another illustrative stent.

FIG. 10 illustrates a side view of another illustrative endoluminal implant 400, such as, but not limited to, a stent. In some instances, the stent 400 may be formed from an elongated tubular member 402. While the stent 400 is described as generally tubular, it is contemplated that the stent 400 may take any cross-sectional shape desired. The stent 400 may have a first, or proximal end 404, a second, or distal end 406, and an intermediate region 408 disposed between the first end 404 and the second end 406. The stent 400 may include a lumen 410 extending from a first opening adjacent the first end 404 to a second opening adjacent to the second end 406 to allow for the passage of food, fluids, etc.

The stent 400 may be expandable from a first radially collapsed configuration (not explicitly shown) to a second radially expanded configuration. In some cases, the stent 400 may be deployed to a configuration between the collapsed configuration and a fully expanded configuration. The stent 400 may be structured to extend across a stricture and to apply a radially outward pressure to the stricture in a lumen to open the lumen and allow for the passage of foods, fluids, air, etc.

The proximal end 404 of the stent 400 may include a plurality of loops 412. The loops 412 may be configured to receive a retrieval tether or suture interwoven therethrough, or otherwise passing through one or more of the loops 412. The retrieval suture may be used to collapse and retrieve the stent 400, if so desired. For example, the retrieval suture may be pulled like a drawstring to radially collapse the proximal end 404 of the stent 400 to facilitate removal of the stent 400 from a body lumen. In some embodiments, the loops 412 may take the form of cathedral or atraumatic style loop ends, as desired.

The stent 400 may have a braided or woven structure, fabricated from a plurality of longitudinal filaments 414 (extending in a direction generally parallel to a longitudinal axis 420 of the stent 400) interwoven with a plurality of helical filaments 416, 418 to form a plurality of open cells 422. The longitudinal filaments 414 may be considered "warp" filaments and the helical filaments 416, 418 may be considered "weft" filaments. As the longitudinal filaments 414 are interwoven with the helical 416, 418 filaments, the longitudinal filaments 414 may undulate or have a sinusoidal wave shape along a length of the stent 400. As will be discussed in more detail herein, the helical filaments 416, 418 may be configured to be looped around the longitudinal filaments 414 in different diagonal directions. In other words, the first helical filament 416 may extend in a first helical (or rotational) direction and the second helical filament 418 may extend in a second helical (or rotational) direction opposite from the first. In some cases, the filaments 414, 416, 418 may be monofilament, while in other cases the filaments 414, 416, 418 may be two or more filaments wound, braided, or woven together. In some instances, an inner and/or outer surface of the stent 400 may be entirely, substantially or partially, covered with a polymeric covering or coating. The covering or coating may extend across and/or occlude one or more, or a plurality of the cells 422 defined by the struts or filaments 414, 416, 418. The covering or coating may help reduce food impaction and/or tumor or tissue ingrowth.

It is contemplated that the stent 400 can be made from a number of different materials such as, but not limited to, metals, metal alloys, shape memory alloys and/or polymers, as desired, enabling the stent 400 to be expanded into shape when accurately positioned within the body. In some instances, the material may be selected to enable the stent 400 to be removed with relative ease as well. For example, the stent 400 can be formed from alloys such as, but not limited to, Nitinol and Elgiloy®. Depending on the material selected for construction, the stent 400 may be self-expanding (e.g., configured to automatically radially expand when unconstrained). In some embodiments, fibers may be used to make the stent 400, which may be composite fibers, for example, having an outer shell made of Nitinol having a platinum core. It is further contemplated the stent 400 may be formed from polymers including, but not limited to, polyethylene terephthalate (PET). In some embodiments, the stent 400 may be self-expanding while in other embodiments, the stent 400 may be expanded by an expansion device (such as, but not limited to a balloon inserted within the lumen 410 of the stent 400). As used herein the term "self-expanding" refers to the tendency of the stent to return to a preprogrammed diameter when unrestrained from an external biasing force (for example, but not limited to a delivery catheter or sheath). The stent 400 may be delivered to a target region within the body using a similar device to that described above with respect to FIGS. 5 and 6. The stent 400 may include a one-way valve, such as an elastomeric slit valve or duck bill valve, positioned within the lumen 410 thereof to prevent retrograde flow of gastrointestinal fluids.

In some instances, in the radially expanded configuration, the stent 400 may include a first end region 424 proximate the proximal end 404 and a second end region 426 proximate the second end 406. In some embodiments, the first end region 424 and the second end region 426 may include retention features or anti-migration flared regions (not explicitly shown) having enlarged diameters relative to the intermediate portion 408. The anti-migration flared regions, which may be positioned adjacent to the first end 404 and the second end 406 of the stent 400, may be configured to engage an interior portion of the walls of the esophagus or other body lumen. In some embodiments, the retention features, or flared regions may have a larger diameter than the cylindrical intermediate region 408 of the stent 400 to prevent the stent 400 from migrating once placed in the esophagus or other body lumen. It is contemplated that a transition from the cross-sectional area of the intermediate region 408 to the retention features or flared regions may be gradual, sloped, or occur in an abrupt step-wise manner, as desired.

In some embodiments, the first anti-migration flared region may have a first outer diameter and the second anti-migration flared region may have a second outer diameter. In some instances, the first and second outer diameters may be approximately the same, while in other instances, the first and second outer diameters may be different. In some embodiments, the stent 400 may include only one or none of the anti-migration flared regions. For example, the first end region 424 may include an anti-migration flare while the second end region 426 may have an outer diameter similar to the intermediate region 408. It is further contemplated that the second end region 426 may include an anti-migration flare while the first end region 424 may have an outer diameter similar to an outer diameter of the intermediate region 408. In some embodiments, the stent 400 may have a uniform outer diameter from the first end 404 to the second end 406. In some embodiments, the outer diameter of the intermediate region 408 may be in the range of 15 to 25 millimeters. The outer diameter of the anti-migration flares may be in the range of 20 to 30 millimeters. It is contemplated that the outer diameter of the stent 400 may be varied to suit the desired application.

It is contemplated that the stent 400 can be made from a number of different materials such as, but not limited to, metals, metal alloys, shape memory alloys and/or polymers, as desired, enabling the stent 400 to be expanded into shape when accurately positioned within the body. In some instances, the material may be selected to enable the stent 400 to be removed with relative ease as well. For example, the stent 400 can be formed from alloys such as, but not limited to, Nitinol and Elgiloy®. Depending on the material selected for construction, the stent 400 may be self-expanding or require an external force to expand the stent 400. In some embodiments, composite filaments may be used to make the stent 400, which may include, for example, an outer shell or cladding made of Nitinol and a core formed of platinum or other radiopaque material. It is further contemplated the stent 400 may be formed from polymers including, but not limited to, polyethylene terephthalate (PET). In some instances, the filaments of the stent 400, or portions thereof, may be bioabsorbable or biodegradable, while in other instances the filaments of the stent 400, or portions thereof, may be biostable.

Figure 11:
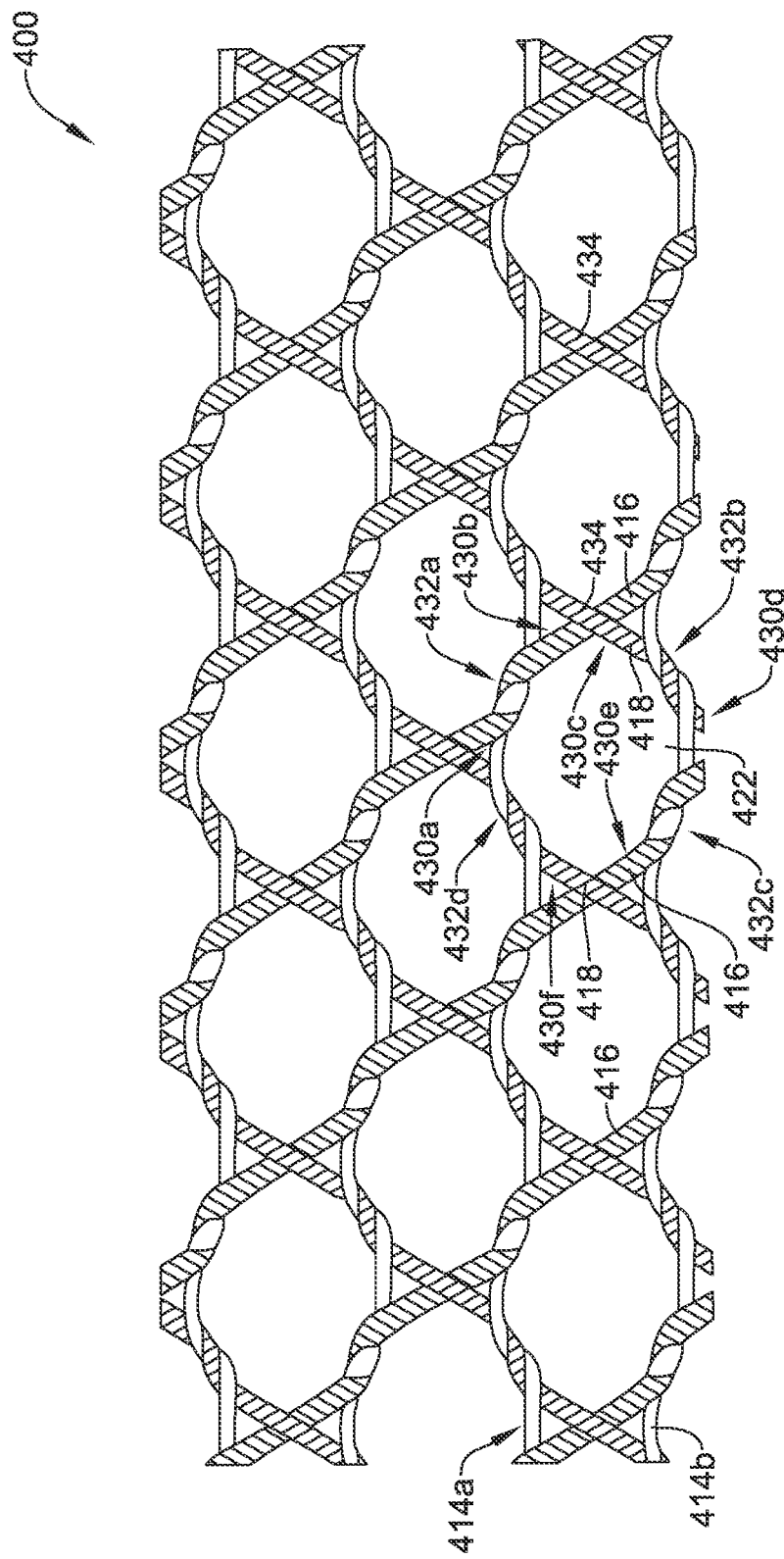
FIG. 11 is a partial enlarged side view of the illustrative stent of FIG. 10.

FIG. 11 illustrates a flat layout of a portion of the illustrative stent 400. As described above the stent 400 is formed from a plurality of elongated strands 414, 416, 418. The strands are wires 414, 416, 418 are woven to form a pattern of geometric cells 422. The sides 430*a*, 430*b*, 430*c*, 430*d*, 430*e*, 430*f* (collectively, 430) of each of the cells 422 are defined by a series of strand lengths. Each of the sides 430 may be joined to an adjoining side in an intersection where two or more of the strands 414, 416, 418 are helically wrapped about each other to form interlocking joints 432*a*, 432*b*, 432*c*, 432*d* (collectively, 432). For example, a first interlocking joint 432*a* may include a helical strand 416 helically wound with a first longitudinal strand 414*a*, a second joint 432*b* may include a second or different longitudinal strand 414*b* helically wound with another helical strand 418. It is contemplated that the helical strands 416, 418 forming the joints 432*a*, 432*b* may extend in opposite rotational directions about the circumference of the stent 400. In some instances, the helical strands 416, 418 may be separate and distinct wires, although this is not required. The third interlocking joint 432*c* may include the second longitudinal strand 414*b* helically wound with the helical strand 416. In some embodiments, the helical strand 416 forming the first interlocking joint 432*a* and the third interlocking joint 432*c* may be the same filament which has made a complete helical rotation about a circumference stent 400, although this is not required. The fourth interlocking joint 432*d* may include the first longitudinal strand 414*a* helically wound with the helical strand 418. In some embodiments, the helical strand 418 forming the second interlocking joint 432*b* and the fourth interlocking joint 432*c* may be the same filament which has made a complete helical rotation about a circumference of the stent 400, although this is not required. The longitudinal strands 414 and helical strands 416, 418 may interact at the interlocking joints 432 such that the interlocking joints 432 have an angle in the range of about 30° to about 60°, 40° to about 50° or approximately 45° relative to a longitudinal axis or plane of the stent 400. In other words, as the helical strands 416, 418 are helically wrapped, the interlocking joints 432 may have a non-parallel or non-orthogonal angle relative to a longitudinal axis or plane of the stent 400.

In some embodiments, the cells 422 may have a generally hexagonal shape. However, the shape of the cell 422 may vary based on the number of interlocking joints 432 forming the cell 422. For example, each cell 422 may not include four interlocking joints 432. It is contemplated that the cell 422 may include fewer than four or more than four interlocking joints 432, as desired. It is further contemplated that some interlocking joints 432 may be shared with an adjacent cell 422. For example, some interlocking joint 432 may be eliminated to reduce the radial force exerted by the stent 400. In some embodiments, each cell 422 may include one or more cross points 434 where the strands 416, 418 cross but are not twisted to form a wrap as at the interlocking joints 432.

It is contemplated that the size of the cells 422 may be controlled based on the number of helical strands 416, 418. For example, the larger the number of helical strands 416, 418 the smaller the cells 422 will be. Said differently a stent having twelve helical strands 416, 418 will have smaller cells 422 than the stent having six helical strands 416, 418. In some cases, both the longitudinal strands 414 and the helical strands 416, 418 may be increased to reduce the size of the cells 422. It is further contemplated that the longitudinal strands 414 may be uniformly spaced about the circumference of the stent 400. This may result in cells 422 having similar sizes. In other embodiments, the longitudinal strands 414 may be positioned with unequal spacing or eccentric spacing about the circumference of the stent 400. This may result in the stent 400 having cells 422 of differing sizes.

The stents, delivery systems, and the various components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic Nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; titanium; combinations thereof; and the like; or any other suitable material.

Some examples of suitable polymers for the stents or delivery systems may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

In at least some embodiments, portions or all of the stents or delivery systems may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of the stents or delivery systems in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents or delivery systems to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent, the stent comprising:
a knitted elongated tubular member radially expandable from a collapsed configuration to an expanded configuration, the knitted elongated tubular member comprising a single filament forming a plurality of rows extending circumferentially around the tubular member;
wherein each row includes a plurality of loops formed from the filament and a plurality of rung portions formed from the filament, wherein one of the rung portions extends between adjacent ones of the loops;
wherein each loop of the plurality of loops includes a loop portion and an overlapping base portion;
wherein each overlapping base portion includes a respective first segment of the filament crossing over a respective second segment of the filament;
wherein each loop portion includes a respective third segment of the filament extending between one of the respective first segments and one of the respective second segments;
wherein a length of the rung portions in the collapsed configuration is less than a length of the rung portions in the expanded configuration.

2. The stent of claim 1, wherein at least some of the plurality of loops in a first row of the plurality of rows are each suspended from one of the loops in a preceding row.

3. The stent of claim 2, wherein at least some of the plurality of loops in the first row of the plurality of rows are each suspended from one of the rung portions of the preceding row.

4. The stent of claim 1, wherein each of the plurality of loops in a first row of the plurality of rows is suspended from one of the loops in a preceding row.

5. The stent of claim 4, wherein each of the plurality of loops in the first row is wrapped about the overlapping base portion of one of the loops in the preceding row.

6. The stent of claim 1, wherein at least some of the plurality of loops in a first row of the plurality of rows are each suspended from one of the rung portions in a preceding row.

7. The stent of claim 1, wherein some of the plurality of rows have a first number of loops and some of the plurality of rows have a second number of loops less than the first number of loops.

8. The stent of claim 1, wherein the elongated tubular member has at least a first longitudinal portion and a second longitudinal portion, the second longitudinal portion having a lower radial force in the expanded configuration than the first longitudinal portion.

9. The stent of claim 1, wherein each loop is a twisted knit stitch of the filament.

10. A stent, the stent comprising:
a knitted elongated tubular member radially expandable from a collapsed configuration to an expanded configuration, wherein the knitted elongated tubular member has a first length in the collapsed configuration and a second length in the expanded configuration, the first length of the knitted elongated tubular member being greater than the second length of the knitted elongated tubular member;
wherein the knitted elongated tubular member comprises a single filament forming a plurality of rows extending circumferentially around the tubular member;
wherein each row includes a plurality of twisted knit stitches formed from the filament and a plurality of rung portions formed from the filament, wherein one of the rung portions extends between adjacent ones of the twisted knit stitches;
wherein each twisted knit stitch includes a loop portion and an overlapping base portion formed of the filament;
wherein each rung portion has a first length in the collapsed configuration and a second length in the expanded configuration, the second length of each rung portion being greater than the first length of each rung portion.

11. The stent of claim 10, wherein when the knitted elongated tubular member transitions from the expanded configuration to the collapsed configuration, a portion of the first length of the rungs is pulled into the loop portions of the twisted knit stiches to lengthen the loop portions.

12. The stent of claim 10, wherein the twisted knit stitches form ridges along an outer surface of the knitted elongated tubular member.

13. The stent of claim 10, wherein at least some of the plurality of twisted knit stitches in a first row of the plurality of rows are each suspended from one of the twisted knit stitches in a preceding row.

14. The stent of claim 13, wherein at least some of the plurality of twisted knit stitches in the first row of the plurality of rows are each suspended from one of the rung portions of the preceding row.

15. The stent of claim 10, wherein each of the plurality of twisted knit stitches in a first row of the plurality of rows is suspended from one of the twisted knit stitches in a preceding row.

16. The stent of claim 15, wherein each of the plurality of twisted knit stitches in the first row includes the loop portion wrapped about the overlapping base portion of one of the twisted knit stitches in the preceding row.

17. The stent of claim 10, wherein at least some of the plurality of twisted knit stitches in a first row of the plurality of rows are each suspended from one of the rung portions in a preceding row.

18. The stent of claim 10, wherein some of the plurality of rows have a first number of twisted knit stitches and some of the plurality of rows have a second number of twisted knit stitches less than the first number of twisted knit stitches.

19. The stent of claim 10, wherein the elongated tubular member has at least a first longitudinal portion and a second longitudinal portion, the second longitudinal portion having a lower radial force in the expanded configuration than the first longitudinal portion.

* * * * *